United States Patent
Linder

Patent Number: 5,819,727
Date of Patent: Oct. 13, 1998

[54] SELF-ILLUMINATING INTRODUCER

[76] Inventor: Gerald S. Linder, P.O. Box 1085, Pacific Palisades, Calif. 90272

[21] Appl. No.: 593,135

[22] Filed: Feb. 1, 1996

[51] Int. Cl.$^6$ ................................................. A61M 16/00
[52] U.S. Cl. ................................ 128/200.26; 128/207.14; 128/207.18; 128/11
[58] Field of Search .................... 128/200.26, 207.14, 128/207.15, 207.18, 772, 11; 600/212, 223

[56] References Cited

U.S. PATENT DOCUMENTS

| | | | |
|---|---|---|---|
| 4,444,185 | 4/1984 | Shugar | 128/200.26 |
| 4,611,579 | 9/1986 | Bellhouse . | |
| 4,655,214 | 4/1987 | Linder | 128/207.18 |
| 4,938,746 | 7/1990 | Etheredge, III et al. | 128/207.18 |
| 4,949,716 | 8/1990 | Chenoweth | 128/207.18 |
| 5,277,173 | 1/1994 | Cantele | 128/11 |

Primary Examiner—Vincent Millin
Assistant Examiner—V. Srivastava
Attorney, Agent, or Firm—Cislo & Thomas LLP

[57] ABSTRACT

A self-illuminating introducer (10) that is inserted into an endotracheal catheter to aid in the intubation of the catheter into the laryngeal and tracheal passageway of a patient. The introducer (10) features a chemiluminescent vial (20) that is attached into and projects from the distal end of an elongated pliable tube (12) or is enclosed within the distal portion of an elongated pliable tube. The vial (20) is made of a pliable plastic having a glass liner (28). The vial contains a liquid reactant (34) and encloses a glass ampule (30) that contains an oxidizer. When the tube (12) is bent or pressed around the area encompassing the vial (20), the vial is also depressed which causes the ampule (30) to break allowing the oxidizer to mix with the reactant to produce a chemiluminescent light that is emitted from the front end of the tube (12). The introducer (10) can also be designed to include an inflatable sheath (50) that when inflated, allows a safer and more comfortable intubation.

21 Claims, 3 Drawing Sheets

SELF-ILLUMINATING INTRODUCER

BACKGROUND OF THE INVENTION

1. Field of the Invention

This invention relates to endotracheal catheters or tubes and more particularly to introducers that facilitate the intubation of catheters or tubes into the patient. Specifically, the present invention is directed to a pliable introducer tube that includes at its front end, a sealed chemiluminesent vial. When the tube is bent or pressed, the vial reacts by emitting a light at the front end of the introducer tube.

2. Description of the Related Art

During the course of many surgical operations; emergency situations, both pre-hospital and hospital; ICU and long term critical care, patients often require endotracheal intubation. This is accomplished by the insertion of an endotracheal catheter or tube. Usually, unless one of the lungs is being operated on, it is desirable to place the distal end of the endotracheal catheter proximally of the junction between the bronchi. Endotracheal intubation can be difficult even for an experienced anesthesiologist; often the endotracheal catheter can be inadvertently placed down the esophagus instead of the windpipe. Moreover, even if the catheter is correctly placed at the onset of an operation, it can become dislodged as a consequence of the movements of the patient during the operative procedures. Thus, it is necessary to periodically determine the location of the endotracheal catheter during an operation.

The positioning of an endotracheal catheter is determined currently by three methods. First, the anesthesiologist listens to the lungs during a lung oxygenation or pressurization step. The sounds heard with a properly placed endotracheal catheter generally differ from the sounds heard with an improper placement. Second, the carbon dioxide content of gases expelled via the endotracheal catheter is measured. If the catheter is properly placed in the trachea, there is carbon dioxide present in the outcoming gases. Third, tissue oxygenation is measured to determine whether the blood is carrying oxygen to the patient's tissues. The tissue oxygenation can be measured from a patient's finger, for example, or other areas of the body that do not interfere with the operation being performed. Although these methods are the most commonly utilized, none are completely effective in determining exact endotracheal catheter placement.

During some operations, fiber optic endoscopes or lighted stylets are inserted into a body cavity to provide a remote image of the body cavity. Due to the ability of the doctor to actually see the placement of the fiber optic endoscope or stylet, proper placement is usually easier to accomplish and maintain in the course of an operation. In recent years, several versions of a fiber optic endoscope or lighted stylet have been introduced. These include: The Fiberoptic Lighted Intubation Stilette (Benson Medical Industries, Inc. Markham, Ontario, Canada), Flexilum (Concept Corporation, Clearwater, Fla.), Tubestat (Concept Corporation), Fiberoptic Lighted Stylet (Fiberoptic Medical Products, Inc., Allentown, Pa.), and the Trachlight. After more than a decade of use, these devices have proven to be an effective and safe method for insertion of an endotracheal tube.

A fiber optic endoscope or a lighted stylet typically includes an insertion section which is adapted to be inserted into a body cavity and an external control section. The insertion section includes a light carrying bundle of optical fibers or other light source, such as a lightbulb, an optical objective lens and a means for carrying an optical image to the control section. The control section includes a light source, processing means for processing the image received and a display source.

In some types of endoscopes, the insertion section of the endoscope can be shaped or bent in a controlled manner, by external manipulation, to guide the endoscope through a body cavity. This allows the insertion section to be maneuvered through the body cavity without causing harm to the patient.

One area of medicine in which an endoscope has found limited use is in the insertion of the previously mentioned endotracheal catheter. This medical procedure, in which the endotracheal catheter is inserted into the trachea, supplies oxygen or anesthetic gases to the lungs. In some cases, endotracheal intubation is difficult to accomplish. The intubation process, if incorrectly performed, may cause injuries to the patient, such as tears and damage to the larynx, trachea, nasopharynx and bronchi. It is apparent that an external visual image and, especially improved illumination, would be helpful for use in these type of medical intubation processes.

The applicant's prior U.S. Pat. Nos. 3,957,055; 4,185,639; and 4,655,214 pertain to improvements in the intubation of endotracheal catheters and tubes.

A search of the prior art did not disclose any patents that read directly on the claims of the instant invention however, the following U.S. patents were considered related:

| U.S. Pat. No. | INVENTOR | ISSUED |
| --- | --- | --- |
| 5,400,771 | Pirak, et al | 28 March 1995 |
| 5,329,940 | Adair | 19 July 1994 |
| 5,285,778 | Mackin | 15 February 1994 |
| 5,277,173 | Cantele | 11 January 1994 |

The U.S. Pat. No. 5,400,771 Pirak, et al patent discloses an endotracheal intubation assembly and related method. During and after insertion of an endotracheal tube into the trachea of a patient, an image is transmitted along the endotracheal tube from a distal end to a proximal end. This transmitted image enables an operator to determine proper placement of the endotracheal tube. Upon determination that an incoming image is different from a stored reference image, an alert signal is automatically issued to an operator. The signal indicates that the distal end of the endotracheal tube has moved from a predetermined position within the patient's trachea.

The U.S. Pat. No. 5,329,940 Adair patent discloses an endotracheal catheter intubation assist device in which an endoscope is utilized. The endoscope provides a visual image as an aid in performing the intubation of an endotracheal tube into a patient's trachea. The assist device includes a handle, a malleable elongated insertion section and an endoscope assembly having a viewing end mounted within the insertion section to provide a visual image of the trachea. In use, the endotracheal catheter is placed around the insertion section and removably attached to the handle for insertion into the trachea. The malleable insertion section can be bent by the attending medical personnel in order to provide a custom fit for the patient. The handle of the assist device is also formed with an oxygen supply conduit for supplying oxygen to the patient during the intubation process. Additionally, the handle includes a suction port for attaching a suction tube for evacuation of the trachea during the intubation process.

The U. S. Pat. No. 5,285,778 Mackin patent discloses an endotracheal catheter that includes a main tube having a proximal end portion and a distal end portion. There is also an inflatable annular sheath disposed on the main tube that is sealed adjacent to the distal end portion. An inflation tube extends from the distal end portion into the cuff. A viewing lens is located on the distal end portion and optically coupled to a first optical fiber extending from the proximal end portion to the distal end portion. An illumination port is located on the distal end portion coupled to a second optical fiber extending from the proximal end portion to the distal end portion. An illumination source is optically coupled to a proximal end of the second optical fiber. The extended insertion of the endotracheal tube and conditions of adjacent tissue can be viewed by means of a viewing device.

The 5,277,173 Cantele patent discloses a chemiluminiscent, disposable laryngoscope. The device comprises a handle portion with an end and a blade portion which is integrally formed on the end of the handle portion. The blade points away from the handle portion substantially perpendicularly. Inside the blade there is disposed a container which, upon activation, provides chemiluminiscent light.

For background purposes and as indicative of the art to which the invention relates, reference may be made to the following remaining patents found in the search and the listed article.

| U.S. Pat. No. | INVENTOR | ISSUED |
| --- | --- | --- |
| 5,370,828 | Ladyjensky | 6 December 1994 |
| 5,067,051 | Ladyjensky | 19 November 1991 |
| 5,029,049 | Ladyjensky | 2 July 1991 |
| 4,976,710 | Mackin | 11 December 1990 |
| 4,846,153 | Berci | 11 July 1989 |
| 4,570,614 | Bauman | 18 February 1986 |

ARTICLE

Airway Management: Principles and Practice/Edited by J. L. Benumof; Copyright 1996 by Mosby-Year Book Inc.

SUMMARY OF THE INVENTION

The invention is concerned with the direct illumination of the larynx as an adjunct to conventional laryngoscopy which utilizes a laryngoscope. Additionally, the invention is also concerned with its use as an indirect transillumination device that is used without a laryngoscope.

The self-illuminating introducer incorporates a chemiluminescent light source at its front end and is designed to be inserted into an endotracheal catheter. The introducer allows the catheter to be formed into a shape that best adapts to a patient's entry cavity. In its most basic design, the self-illuminating introducer consists of:

1. An elongated, pliable tube having an open front end and rear end,
2. A chemiluminescent vial having a front end, a rear end and a diameter that permits the vial to be inserted into the front end of the pliable tube. When inserted, the front end of the vial is positioned distal to the front end of the pliable tube,
3. Means for retaining the vial within the pliable tube. When the vial is retained and the pliable tube is sufficiently bent or pressed around the area encompassing the vial, the chemiluminescent light is produced from the vial and is then emitted from the front end of the pliable tube and,
4. Means for terminating the rear end of the pliable tube.

The elongated, pliable tube can be constructed of a plastic or metal. In all cases, the front end of the tube is open and the rear end of the tube can be terminated in a sealed loop. The rear end can also be terminated in a terminating assembly that includes a coupler that couples the rear end of the pliable tube to the front end of a terminating tube. The rear end of the terminating tube is attached to a receptacle to which is attached a syringe or the like that controls the flow of fluid.

Into the front end of the pliable tube is inserted the chemiluminescent vial. This vial encloses a quantity of a liquid reactant together with a glass ampule that contains an oxidizer. When the pliable tube is bent or pressed, as described above, the vial alters its shape which causes the glass ampule to break. The breakage of the ampule allows the oxidizer to mix with the reactant which then produces the chemiluminescent light for approximately five minutes.

The introducer is presented in a preferred embodiment that is disclosed in seven design configurations; The first design uses a pliable tube that is made of plastic and incorporates the chemiluminescent vial at its front end. The back end of the pliable tube terminates in a closed loop. The second design is similar to the first but employs a pliable tube that is made of metal in lieu of a plastic tube. The third design is also similar to the first design but further includes a pliable wire that is inserted into the pliable tube. The fourth design utilizes a plastic pliable tube and incorporates a sheath. The pliable tube has an air-vent bore through which a fluid is inserted, by a syringe or the like, to expand the sheath. The rear end of the pliable tube terminates at the terminating assembly, as described above, that couples the rear end of the terminating tube with a receptacle to which is attached the fluid applying syringe or the like. The fifth design is similar to the fourth with the exception that a metal pliable tube is used. The sixth design is similar to the fourth design but it utilizes a metal tube that is inserted into a plastic pliable tube. The front end of the metal tube is located near the air-vent bore and its rear end extends approximately to the rear end of the pliable tube. The seventh design is similar to the sixth with the exception that a plastic tube is inserted into a pliable tube made of metal.

OBJECTS OF THE INVENTION

The primary object of the invention is to provide an introducer that incorporates a chemiluminescent vial that when activated produces a temporary light that aids in the intubation of an endotracheal catheter.

In addition to the primary object of the invention it is also an object to provide a self-illuminating introducer that:

is particularly suitable for use during an emergency situation where a primary light source is not available, provides a pliable introducer that may be sterilized completely for use during an operation, provide an introducer for a catheter that includes an integral chemiluminescent light source, distal to the introducer's front tip, reduces trauma and injury to a patient through use of a distal inflatable sheath as well as offering better means by which catheters may be controllably articulated prior to and during intubation, has a pliable introducer tube which enables a physician to more readily intubate a catheter and then remove the introducer once the introducer is deflated, and is cost effective from both a manufacturer and consumer points of view.

These and other objects and advantages of the present invention will become apparent from the subsequent detailed description of the preferred embodiment and the appended claims taken in conjunction with the accompanying drawings.

DESCRIPTION OF THE PREFERRED EMBODIMENT

Figure 1:
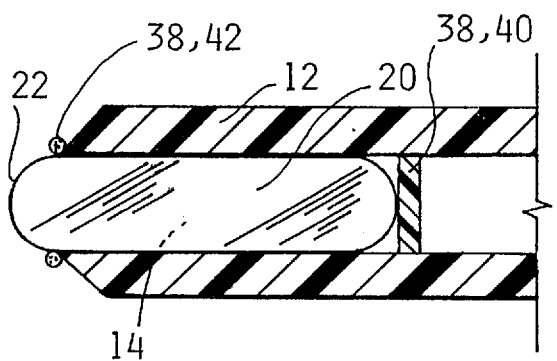
FIG. 1 is a sectional side view of a self-illuminating introducer that uses an elongated pliable tube made of plastic that encloses at its front end a chemiluminescent vial and that terminates in a sealed loop.
Figure 1:
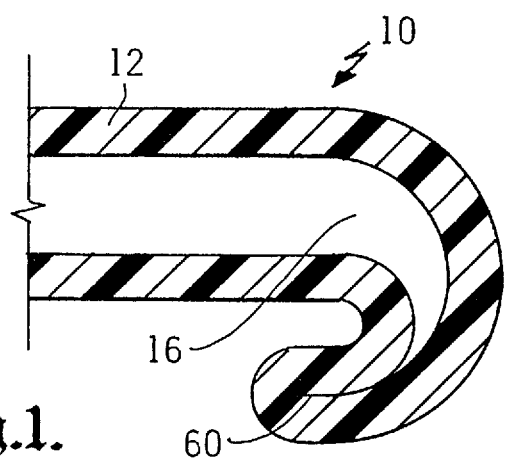

The best mode for carrying out the self-illuminating introducer 10 is presented in terms of a preferred embodiment that is disclosed in seven design configurations. The preferred embodiment, as shown in FIGS. 1–9 is comprised of the following major elements: an elongated, pliable tube 12, a chemiluminescent vial 20, a sealed glass ampule 30, a vial retaining means 38, an opaque sheath 44, an elongated, cylindrical inflatable sheath 50, and a rear terminating assembly 68.

The elongated, pliable tube 12 can be made of a plastic material, such as polyvinyl chloride (PVC) a metal or metal alloy. An annealed 3003 aluminum is preferred as aluminum generates a noncorrosive and inert external layer of aluminum oxide. The aluminum oxide layer prevents any corrosion from taking place upon the pliable tube 12. Other pliable or ductile, metals, alloys, or materials may be used as long as they are sterilized for use in the operating room. Metals, such as copper, may require a coating of plastic over any exposed surface to prevent an adverse reaction from the metal and its surrounding environment.

The length of the pliable tube 12 is determined by the length of the endotracheal catheter into which the pliable tube is inserted. The diameter of the pliable tube 12 must be less than the inside diameter of the catheter. Preferably, the pliable tube 12 has relatively thick walls while maintaining an unobstructed channel for fluid flow therethrough. While allowing a significant amount of bending, the thick-walled and small-channeled pliable tube 12 demands less fluid for inflating the sheath 50 (as described infra). Additionally, the relatively thick walls of the pliable tube 12 prevent it from buckling during bending or other configuration processes.

Figure 2:
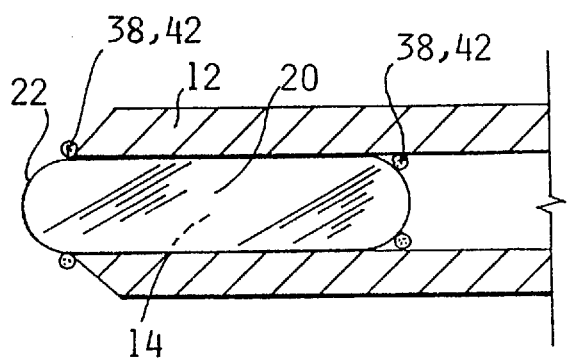
FIG. 2 is a sectional side view of a self-illuminating introducer similar to the introducer of FIG. 1 but uses a pliable tube made of metal.
Figure 2:
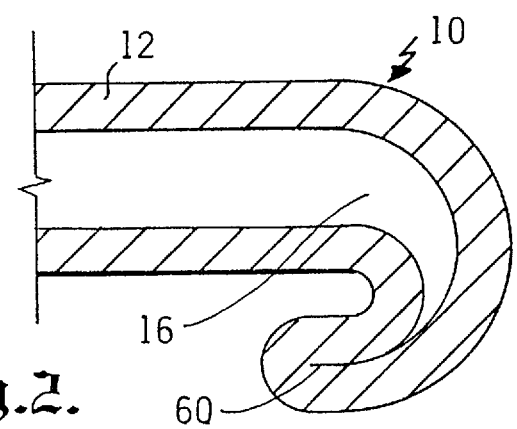
Figure 3:
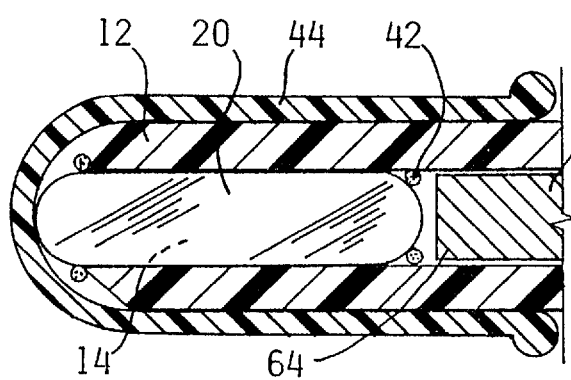
FIG. 3 is a sectional side view of a self-illuminating introducer that uses a plastic elongated, pliable tube in combination with a pliable wire that extends from the rear end of a chemiluminescent vial to the rear end of the pliable tube.
Figure 3:
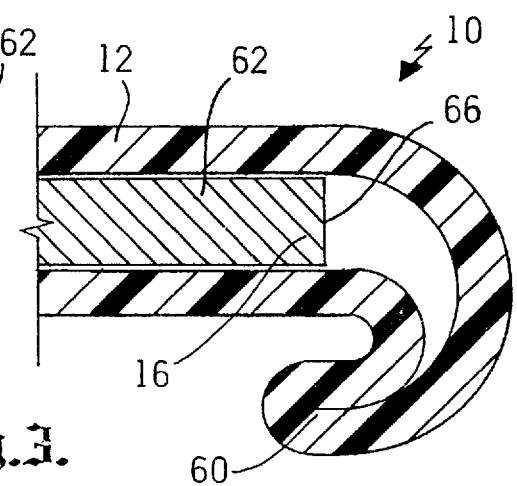

In all cases, the pliable tube 12 has an open front end 14 and a rear end 16. The rear end is sealed when the introducer is terminated with a sealed loop 60 as shown in FIGS. 1–3 or open as shown in FIGS. 4–7 in which case, the open end terminates with a rear terminating assembly 68 as shown in FIG. 8.

Figure 9:
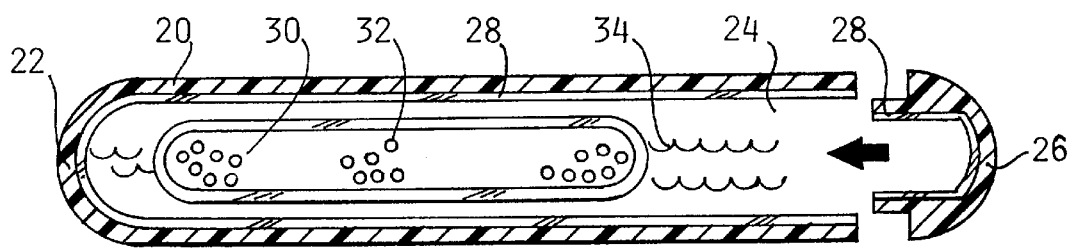
FIG. 9 is a sectional view of the chemiluminescent vial.

All the designs of the self-illuminating introducer 10 utilize a chemiluminescent vial 20 as shown attached in FIGS. 1–7 and separated in FIG. 9. The vial 20 is made of a pliable plastic having a think, glass liner 28 and has a sealed front end 22, an open rear end 24 and a diameter that allows it to be inserted into the open front end 14 of the pliable tube 12 as shown in FIGS. 1–7. When so inserted, the front end 22 of the vial is positioned distal to the front end 14 of the pliable tube 12.

The chemiluminescent vial 20 is further comprised of a glass lined end cap 26 and a sealed glass ampule 30 containing an oxidizer 32 such as an 85 percent solution of hydrogen peroxide in dimethyl phthalate and a catalytic quantity of catalyst such as sodium salicylate. The ampule is inserted into the open rear end 24 of the vial together with a chemiluminescent light-producing liquid reactant 34 such as bis (2,4,5-trichloro-6-carbopentoxyphenyl) oxalate and a fluorescer in dibutyl phthalate. After the insertion of the ampule 30 and reactant 34, the rear end 24 of the vial 20 is sealed with the end cap 26. The end cap is preferably attached by spin welding process that is well known in the art and therefore not described. When the elongated, pliable tube 12 is bent or pressed around the area encompassing the vial 20, the bending and/or pressing causes the vial 20 to alter its shape. This altered shape causes the sealed glass ampule 30 to break facilitating the oxidizer 32 to mix with the liquid reactant 34, producing the chemiluminescent light that is emitted from the front end 14 of the pliable tube 12. The illumination from the vial 20 is expected to last for approximately five minutes, which provides more than the minimal amount of time necessary for insertion of the catheter into a patient.

The vial 20 is retained within the pliable tube 12 by a vial retaining means 38. This means can consist of a friction fitted ring 40 that is inserted into the pliable tube 12, prior to the insertion of the vial 20, as shown in FIG. 1, or preferably a full or segmented adhesive ring 42 as shown in FIGS. 2–7 can be utilized. The ring of adhesive is placed around the rear end 24 of the vial 20 and the interfacing surface of the pliable tube 12. To complete the attachment of the chemiluminescent vial 20, a ring of adhesive 42 is placed around the front end 22 of the vial 20 and the contact surface of the tube 12.

Figure 4:
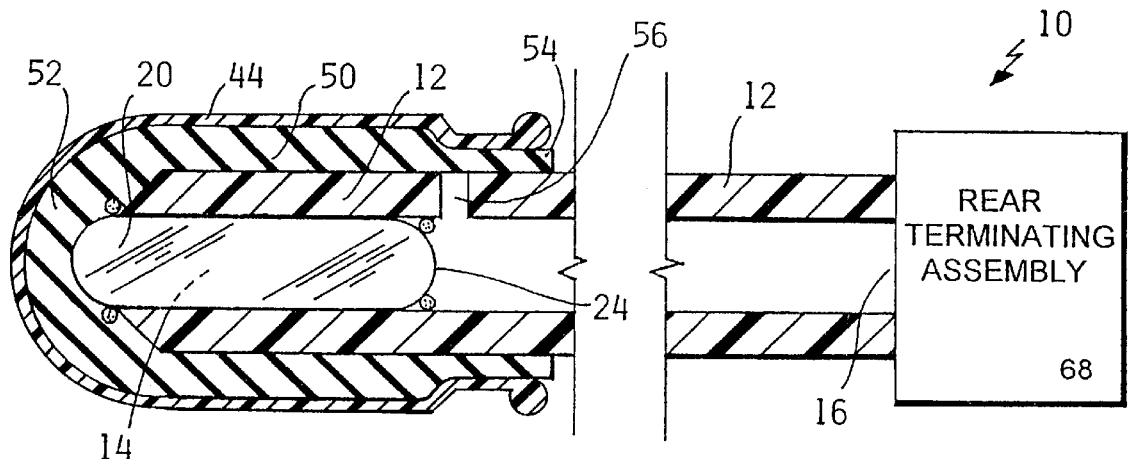
FIG. 4 is a sectional side view of a self-illuminating introducer that incorporates a plastic tube that encloses a chemiluminescent vial, an inflatable sheath an opaque sheath and a rear terminating assembly that includes a terminating tube, a coupler, a receptacle and a clamp.

The illumination time of the chemiluminescent vial 20 will be reduced if the vial is exposed to direct light. Therefore, to enhance the illumination time of the vial 20, an opaque sheath 44 is placed over the elongated pliable tube 12 as shown in FIG. 3, or over the elongated, cylindrical inflatable sheath 50, as shown in FIG. 4. Typically, the opaque sheath 44 consists of a black plastic material that is approximately two to three times longer than the vial 20. A user will open a sterile packet and then slip off the opaque sheath 44 that is covering the end of the introducer 10.

To enhance the utility of the invention, an elongated, cylindrical, inflatable sheath 50 having a rounded front end 52 and a rear end 54 is utilized. The sheath 50 is dimensioned to surround and enclose the outside front section of the pliable tube 12, as shown in FIGS. 4–7. The rear end 54 of the sheath 50 incorporates a fluidtight seal that exists between the inside of the sheath and the outside of pliable tube 12. The sheath 50 is constructed of a relatively thin material such as polyisoprene, latex rubber, polyvinyl chloride, or a similar medically approved material.

The sheath 50 is designed to be inflated by a fluid means supplied under pressure through the pliable tube 12. A fluid means is intended to include any non-toxic fluid, and while such fluids may include saline solutions, nitrogen or other inert gas or gas mixture, the use of such exotic fluids may be complicated and costly. Therefore, the preferred inflation fluid is air, supplied ambient to the patient, as it is readily available and adequate for surgical purposes. The air is applied into the sheath 50 through an air-vent bore 56. The bore is located between the rear end 24 of the vial 20 and the rear end 54 of the sheath as shown in FIGS. 4–7. When the sheath 50 is inflated, it expands and produces a soft tip that allows safer and more comfortable intubation.

As previously discussed, the preferred embodiment of the self-illuminating introducer 10 is disclosed in seven designs. In the first design as shown in FIG. 1, the elongated pliable tube 12 is made of a plastic. The rear end 16 of the tube 12 terminates in a sealed loop 60. The second design as shown in FIG. 2, is similar to the first design with the exception that the pliable tube 12 is made of a metal.

In the third design, a pliable wire 62 that is preferably made of copper, is inserted into the pliable tube 12 which is made of plastic. The wire 62 has a first end 64 and a second end 66. As shown in FIG. 3, the first end 64 of the wire is positioned adjacent the rear adhesive ring 42, and the second end 66 of the wire extends to a position near the rear end 16 of the pliable tube 12. As with the first and second design, the pliable tube 12 of the third design terminates in a sealed loop 60.

In the fourth design, as shown in FIG. 4, a pliable tube 12 made of plastic, is utilized with an attached inflatable sheath 50. In this design, the pliable tube 12 has an air-vent bore 56 that allows the sheath 50 to be filled with air. The rear end 16 of the pliable tube 12 terminates at a rear terminating assembly 68 that consists of a terminating tube 70, a coupler 76, a receptacle 82 and a clamp 88, as shown in FIG. 8.

A terminating tube 70 is preferably made of plastic and includes a front end 72 and a rear end 74. The coupler 76 is constructed of a rubber material and has a front end 78 and a rear end 80. Into the front end 78 of the coupler 76 is inserted the rear end 16 of the pliable tube 12 and into the rear end 80 of the coupler is inserted the front end 72 of the terminating tube 70. The receptacle 82 has a front end 84 and a rear end 86. Into the receptacle's front end 84 is inserted the rear end 74 of the terminating tube 70 and into the rear end 86 of the receptacle 82 is connected a conventional medical syringe that is used to apply fluid into the inflatable sheath 50 via the pliable tube 12. As also shown in FIG. 8, a pliable clamp 88 is placed between the front end 72 and rear end 74 of the terminating tube 70. The clamp controls the fluid flow that is applied to expand the inflatable sheath 50.

Figure 5:
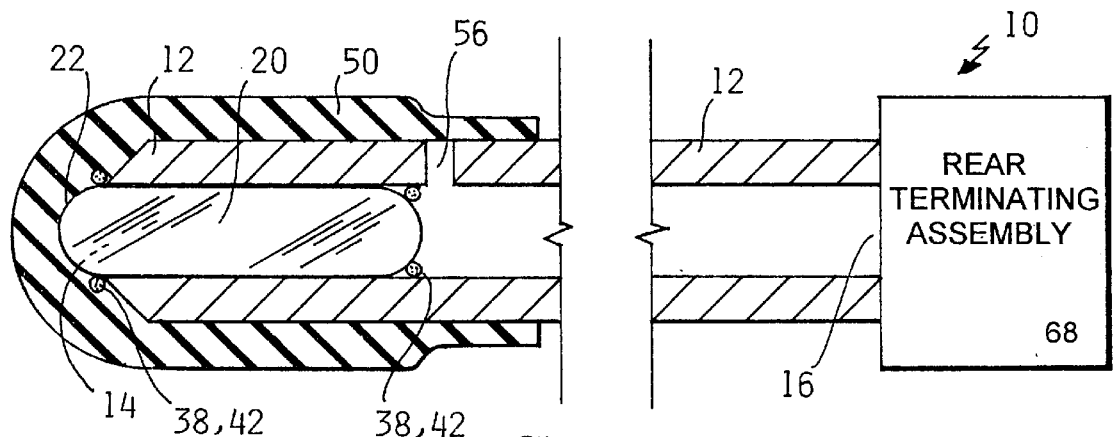
FIG. 5 is a sectional side view of a self-illuminating introducer that uses a metal tube to enclose a chemiluminescent vial, an inflatable sheath and that terminates in a rear terminating assembly.

The fifth design as shown in FIG. 5, utilizes a pliable tube 12 made of metal that has attached a sheath 50 that is inflated by means of the air-vent bore 56. The rear end 16 of the metal pliable tube 12 terminates at a rear terminating assembly 68 as described supra.

Figure 6:
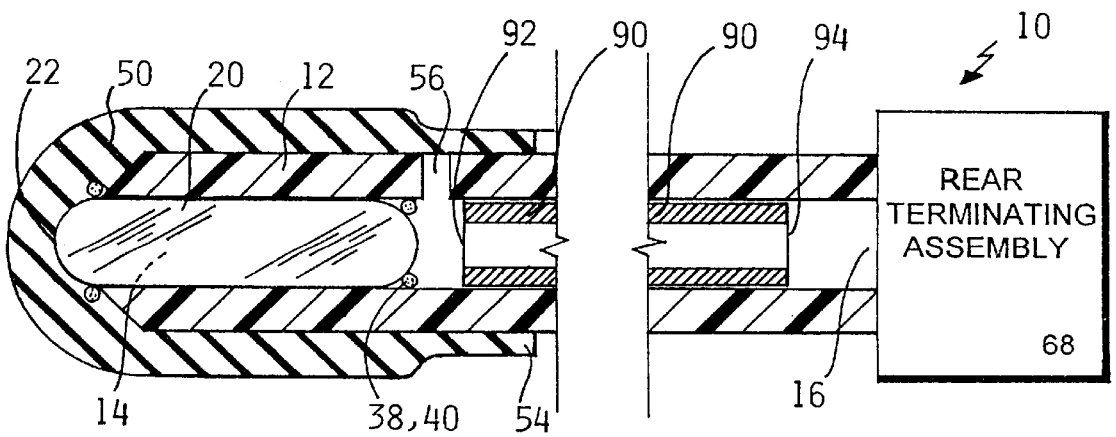
FIG. 6 is a sectional side view of a self-illuminating introducer similar to the introducer of FIG. 4 but that includes a pliable metal tube inserted through the pliable plastic tube.

The sixth design as shown in FIG. 6, is similar to the fourth design shown in FIG. 4. The sixth design further includes a pliable metal tube 90 having a first end 92 and a second end 94. The metal tube 90 is inserted into the pliable tube 12 with the front end 92 of the metal tube 90 positioned near the air-vent bore 56. The second end 94 extends into the pliable tube 12 for approximately one-third the length of the pliable tube 12.

Figure 7:
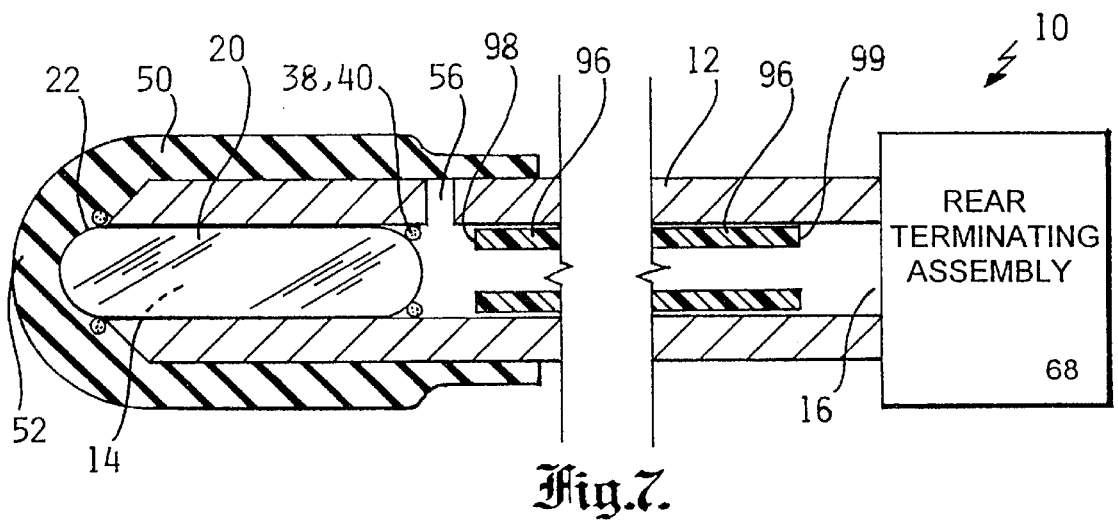
FIG. 7 is a sectional side view of a self-illuminating introducer similar to the introducer of FIG. 5 but that includes a pliable plastic tube inserted through the metal pliable tube.
Figure 8:
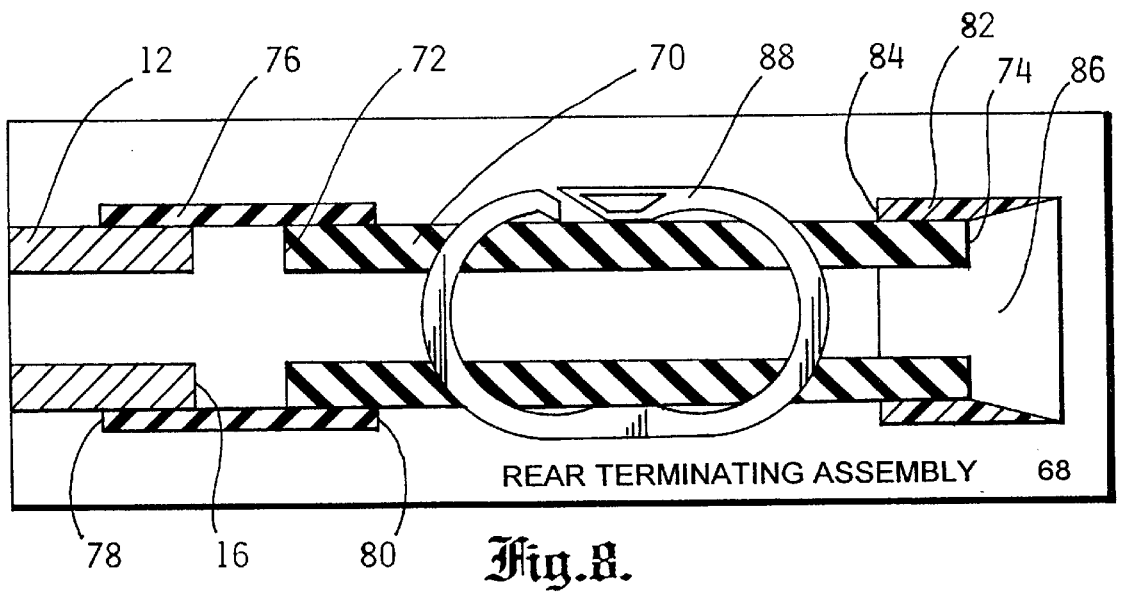
FIG. 8 is a side sectional view of the rear terminating assembly as used with the introducer of FIGS. 4, 5, 6 and 7.

The seventh design as shown in FIG. 7, is similar to the fifth design, as shown in FIG. 5. The seventh design further includes a pliable plastic tube 96 having a first end 98 and a second end 99. The pliable plastic tube 96 is inserted into the metal pliable tube 12 with the first end 98 of the tube 96 positioned near the air-vent bore 56. The second end 99 extends into the pliable tube 12 for approximately one-third the length of the pliable tube 12.

While the invention has been described in complete detail and pictorially shown in the accompanying drawings it is not to be limited to such details, since many changes and modifications may be made in the invention without departing from the spirit and scope thereof. Hence, it is described to cover any and all modifications, compounds and forms which may come within the language and scope of the appended claims.

What I claim is:

1. A self-illuminating introducer for insertion into an endotracheal catheter, said introducer comprising:
   a) an elongated, pliable tube having an open front end and rear end,
   b) a chemiluminescent vial having a front end, a rear end and a diameter that allows said vial to be inserted into the front end of said pliable tube with the front end of said vial positioned distal to the front end of said pliable tube,
   c) means for retaining said vial within said pliable tube comprising at least a ring of adhesive around the front end of said vial for sealingly and fixedly adhering said vial to said open front end of said elongated pliable tube, whereupon, when said pliable tube, is sufficiently bent or pressed, around the area encompassing said vial, said vial produces a chemiluminescent light that is emitted from the front end of said pliable tube,
   d) means for terminating the rear end of said pliable tube,
   e) the introducer further comprising an elongated, cylindrical, inflatable sheath having a front end and a rear end, where said sheath surrounds and enclosed the front end of said pliable tube.

2. The introducer as specified in claim 1 wherein said pliable tube is made of a plastic having a relatively thick wall to prevent buckling during use.

3. The introducer as specified in claim 2 wherein said plastic is polyvinyl chloride (PVC).

4. The introducer as specified in claim 1 wherein said pliable tube is made of a metal or an alloy having a relatively thick wall to prevent buckling during use.

5. The introducer as specified in claim 4 wherein said metal is aluminum.

6. The introducer as specified in claim 1 wherein said means for retaining said vial comprises:
   a) a ring of adhesive placed around the rear end of said vial and the interfacing surface of said pliable tube, and
   b) a ring of adhesive placed around the front end of said vial and the contact surface of said pliable tube.

7. A self-illuminating introducer for insertion into an endotracheal catheter, said introducer comprising:
   a) an elongated, pliable tube having an open front end and rear end, b) a chemiluminescent vial having a front end, a rear end and a diameter that allows said vial to be inserted into the front end of said pliable tube with the front end of said vial positioned distal to the front end of said pliable tube, c) means for retaining said vial within said pliable tube, whereupon, when said pliable tube, is sufficiently bent or pressed, around the area encompassing said vial, said vial produces a chemiluminescent light that is emitted from the front end of said pliable tube and, d) means for terminating the rear end of said pliable tube, said chemiluminescent vial further comprises:

e) a sealed glass ampule containing an oxidizer, f) said vial made of a pliable plastic having an inner glass liner and having a sealed front end and an open rear end, where into the open rear end of said vial is inserted said sealed glass ampule and a liquid reactant, g) an end cap that is attached by an attachment means to the open rear end of said vial after the insertion of said ampule and reactant, whereupon when said elongated, pliable tube is bent or pressed, around the area encompassing said vial, the bending and/or pressing causes said plastic vial to deform which causes said glass ampule to break facilitating the oxidizer to mix with the reactant, producing the chemiluminescent light that is emitted from the front end of said pliable tube, and e) the introducer further comprising an elongated, cylindrical, inflatable sheath having a front end and a rear end, where said sheath surrounds and encloses the front end of said pliable tube.

8. The introducer as specified in claim 7 wherein said oxidizer consists of an 85 percent solution of hydrogen peroxide in dimethyl phthalate and a catalytic quantity of catalyst such as sodium salicylate.

9. The introducer as specified in claim 8 wherein said liquid reactant consists of bis (2,4,5-trichloro-6-carbopentoxyphenyl) oxalate and a fluorescer in dibutyl phthalate.

10. The introducer as specified in claim 9 further comprising an opaque sheath dimensioned to be inserted into the front end of said elongated, plastic tube over the area encompassing said chemiluminescent vial, where said opaque sheath protects said vial from direct or stray light.

11. The introducer as specified in claim 7 further comprising:
an air-vent bore located between the rear end of said vial and the rear end of said sheath, where said bore allows an applied air to flow into and expand said inflatable sheath.

12. The introducer as specified in claim 7 further comprising:
a) an elongated, cylindrical, inflatable sheath having a front end and a rear end, where said sheath surrounds and encloses the outside front section of said pliable tube, and
b) an air-vent bore located between the rear section of said vial and the rear end of said sheath where said bore allows an applied air to flow into and expand said inflatable sheath.

13. The introducer as specified in claim 7 wherein the rear end of said pliable tube terminates in a sealed loop.

14. The introducer as specified in claim 7 further comprising a pliable wire having a first end and a second end, where said wire is inserted into said pliable tube with the first end of said wire positioned adjacent the rear adhesive ring and the second end of said wire extends to a position near the rear end of said pliable tube.

15. The introducer as specified in claim 14 wherein said pliable wire is made of copper.

16. The introducer as specified in claim 14 wherein the rear end of said pliable tube and the second end of said pliable wire terminate in a sealed loop.

17. The introducer as specified in claim 11 wherein the rear end of said pliable tube terminates at a rear terminating assembly comprising:
a) a pliable, terminating tube having a front end and rear end,
b) a coupler having a front end and rear end, where into the front end of said coupler is inserted the rear end of said pliable tube, and into the rear end of said coupler is inserted the front end of said terminating tube,
c) a receptacle having a front end and a rear end, where into the front end of said receptacle is inserted the rear end of said terminating tube and into the rear end of said receptacle is connected a conventional medical syringe, and
d) a pliable clamp placed between the front and rear ends of said pliable terminating tube.

18. The introducer as specified in claim 12 wherein the rear end of said pliable tube terminates at a rear terminating assembly comprising:
a) a pliable, terminating tube having a front end and a rear end,
b) a coupler having a front end and rear end, where into the front end of said coupler is inserted the rear end of said pliable tube, and into the rear end of said coupler is inserted the front end of said terminating tube,
c) a receptacle having a front end and a rear end, where into the front end of said receptacle is inserted the rear end of said terminating tube and into the rear end of said receptacle is connected a conventional medical syringe, and
d) a pliable clamp placed between the front and rear ends of said pliable terminating tube.

19. The introducer as specified in claim 17 further comprising a pliable metal tube having a first end and a second end, where said metal tube is inserted into said plastic pliable tube with the first end of said metal tube positioned near the air-vent bore and the second end of said metal tube extends into said plastic pliable tube for substantially one-third the length of said pliable tube.

20. The introducer as specified in claim 17 further comprising a pliable plastic tube having a first end and second end, where said plastic tube is inserted into said metal pliable tube with the first end of said plastic tube positioned near the air-vent bore and the second end of said plastic tube extends into said metal pliable tube for substantially one-third the length of said pliable tube.

21. A self-illuminating introducer for insertion into an endotracheal catheter to aid the intubation of the catheter into the laryngeal and tracheal passageway of a patient, said introducer comprising:
a) an elongated pliable tube having an open front end and a rear end,
b) a chemiluminescent vial comprising:
(1) a sealed glass ampule containing an oxidizer,
(2) said vial made of a pliable plastic having a glass liner and having a sealed front end and an open rear end, where into said vial's open end is inserted said sealed glass ampule and a liquid reactant,
(3) an end cap that is attached by an attachment means to the open rear end of said vial after the insertion of said ampule and reactant, wherein said vial has a diameter that allows said vial to be inserted into the front end of said pliable tube with said vials' front end positioned distal to the front end of said pliable tube, c) means for retaining said vial within said pliable tube, whereupon when said elongated, pliable tube is sufficiently bent or pressed, around the area encompassing said vial, the bending and/or pressing causes said plastic vial to deform which causes said glass ampule to break facilitating the oxidizer to mix with the reactant producing the chemiluminescent light to be emitted from the front end of said pliable tube, d) an elongated, cylindrical, inflatable sheath having a front end and a rear end, where said sheath surrounds and encloses the front end of said pliable tube, e) an air vent bore located between the rear end of said vial and the rear end of said sheath, where said bore allows fluid of sufficient pressure to expand said sheath to a diameter at least as large as the inside diameter of said endotracheal catheter to further produce a smooth rounded protrusion that extends beyond the front end of said elongated pliable tube and for entry into the laryngotracheal passageway of the patient, f) a structure for terminating the rear end of said pliable tube, said structure comprising:
  (1) a pliable, terminating tube having a front end and a rear end,
  (2) a coupler having a front end and rear end, where into the front end of said coupler is inserted the rear end of said pliable tube, and into the rear end of said coupler is inserted the front end of said terminating tube,
  (3) a receptacle having a front end and a rear end, where into the front end of said receptacle is inserted the rear end of said terminating tube and into the rear end of said receptacle is connected a conventional medical syringe, and
  (4) a pliable clamp placed between the front end and rear ends of said pliable terminating tube.

* * * * *